(12) United States Patent
Landgraf

(10) Patent No.: US 9,726,637 B2
(45) Date of Patent: Aug. 8, 2017

(54) GAS ANALYZER WITH FUEL CELL (71) Applicant: Bruker Daltonik GmbH, Bremen (DE)

(72) Inventor: Jürgen Landgraf, Gutenberg (DE)

( * ) Notice: Subject to any disclaimer, the term of this patent is extended or adjusted under 35 U.S.C. 154(b) by 0 days.

(21) Appl. No.: 14/994,341

(22) Filed: Jan. 13, 2016

(65) Prior Publication Data
US 2016/0209362 A1    Jul. 21, 2016

(30) Foreign Application Priority Data

Jan. 15, 2015 (EP) .................................. 15151254

(51) Int. Cl.
| | | |
|---|---|---|
| *H01J 49/24* | (2006.01) | |
| *G01N 27/62* | (2006.01) | |
| *H01J 49/00* | (2006.01) | |
| *H01M 8/04007* | (2016.01) | |
| *H01M 8/04664* | (2016.01) | |
| *H01M 8/04701* | (2016.01) | |
| *F28D 21/00* | (2006.01) | |
| *F28F 13/00* | (2006.01) | |

(52) U.S. Cl.
CPC ........ *G01N 27/622* (2013.01); *H01J 49/0022* (2013.01); *H01J 49/24* (2013.01); *H01M 8/04007* (2013.01); *H01M 8/04664* (2013.01); *H01M 8/04701* (2013.01); *F28D 2021/0043* (2013.01); *F28F 2013/005* (2013.01)

(58) Field of Classification Search
USPC ........................................................ 250/288
See application file for complete search history.

(56) References Cited

U.S. PATENT DOCUMENTS

| | | | | |
|---|---|---|---|---|
| 5,313,061 A | * | 5/1994 | Drew | .................. B01D 59/44 250/281 |
| 6,370,878 B1 | | 4/2002 | Dean et al. | |
| 7,579,589 B2 | * | 8/2009 | Miller | ................ G01N 30/7206 250/281 |
| 7,770,407 B1 | | 8/2010 | Haskell | |
| 8,361,668 B2 | * | 1/2013 | McLean | ............ H01M 8/04201 429/120 |
| 8,394,642 B2 | * | 3/2013 | Jovanovich | .......... G01N 27/745 422/50 |
| 2002/0182462 A1 | | 12/2002 | Ballantine et al. | |
| 2004/0227073 A1 | | 11/2004 | Krasnobaev et al. | |
| 2005/0074645 A1 | * | 4/2005 | Fattic | ...................... H01J 45/00 429/429 |
| 2009/0189064 A1 | | 7/2009 | Miller et al. | |
| 2014/0193734 A1 | | 7/2014 | Ludwiszewski et al. | |
| 2015/0249001 A1 | * | 9/2015 | Piper | ...................... G01N 1/02 250/282 |

FOREIGN PATENT DOCUMENTS

| | | |
|---|---|---|
| DE | 69028304 A1 | 4/1997 |
| DE | 10158512 A1 | 8/2002 |
| EP | 0959512 A1 | 11/1999 |

OTHER PUBLICATIONS

Wikipedia: Fuel Cell [online]. https://en.wikipedia.org; version 07:17 Jan. 13, 2015, accessed Feb. 8, 2017.

* cited by examiner

*Primary Examiner* — Phillip A Johnston
(74) *Attorney, Agent, or Firm* — Benoit & Côté Inc.

(57) ABSTRACT

The invention relates to gas analyzers, especially mobile ion mobility spectrometers or mass spectrometers which are operated at atmospheric pressure to detect dangerous substances. The invention uses a fuel cell to generate the electric operating power of the gas analyzer, and the waste heat from the fuel cell is used to regulate the temperature of modules of the gas analyzer.

15 Claims, 3 Drawing Sheets

GAS ANALYZER WITH FUEL CELL

BACKGROUND OF THE INVENTION

Field of the Invention

The invention relates to gas analyzers, especially gas analyzers for mobile use, with a fuel cell to generate the electrical operating energy.

Description of the Related Art

Ion mobility spectrometers (IMS) and mass spectrometers (MS), which are also collectively referred to as gas analyzers hereinafter, are used in both the civil and the military sector for detecting dangerous or prohibited target substances on surfaces or in the ambient air. The ion mobility analyzers and mass analyzers used in the gas analyzers here can be coupled to gas chromatography devices or other analyzers, e.g. infrared spectrometers.

For the above-mentioned applications, ion mobility spectrometers are usually operated at ambient pressure, their distinguishing feature being a simple and compact design, which means they can be used in large numbers and as mobile detection devices. In an ion mobility spectrometer, the substances to be detected (target substances) and interfering and background substances are usually ionized by chemical ionization (APCI=Atmospheric Pressure Chemical Ionization). Electric fields then cause the ions to move in a drift gas, where they are separated on account of their ion mobility or the field-strength dependence of their ion mobility, and are detected in an ion detector. In contrast, in a mass spectrometer, for example a 2D or 3D Paul ion trap or a quadrupole filter, the ions of the substances to be detected are transferred into the vacuum and analyzed there according to their mass-to-charge ratio.

Due to the increasing terrorist threat the detection of explosives and chemical warfare agents has become very important not only in the military sector but also for homeland security (civil defense). The task, on the one hand, is to prevent their illegal import and attacks on transport means such as planes or ships. On the other hand, homeland security is increasingly also being extended to public buildings and means of transport at home. In addition to the threats posed by explosive substances and chemical warfare agents, there remains the task of detecting drugs as they are being smuggled across national borders. This particularly results in a greatly increasing demand for detection devices at airports, seaports and border control points, where the illegal or hazardous target substances are transported in items of baggage as well as in industrial containers. A further civil application consists in monitoring industrial sites and buildings for leaking chemical pollutants and use by the fire service for detecting harmful chemicals in traffic accidents, ship collisions or fires.

A special challenge is the detection of drugs and explosives in transport containers, for example in suitcases at airports, shipping containers at seaports or vehicles during vehicle spot-checks. The detection of modern explosives, and drugs also, is hampered by the fact that these substances have a very low vapor pressure and are also often sealed in transport containers. In most cases, this means direct detection in the ambient air is possible only if a large sample volume is taken and the substances from the sample are enriched. However, when the target substances are being packed, minimal traces contaminate the surfaces of the baggage items, the transport containers and the clothes and skin of the persons packing the substances. The target substances themselves are present as condensed vapors on the surface itself or on any particles adhering to the surface, but the vapor pressure they develop is too low to allow direct detection in the ambient air.

Owing to the low vapor pressure, the surfaces to be examined are usually wiped with a sampler (made of paper or a Teflon-coated glass-fiber fabric, for example), which causes condensed target substances and any particles carrying target substances to be removed from the surface and to adhere to the sampler. The sampler with the target substances is transferred into a desorption device of a gas analyzer, where it is heated in order to achieve a vapor pressure for the target substances which is sufficient for detection. It is also possible to press a heated probe directly onto the surface under examination and to pass the vapors released in the process to the gas analyzer.

The substances present in the gaseous phase due to desorption or the appropriate vapor pressure (target substances as well as interfering and background substances) can condense in the interior of the gas analyzer and interfere with subsequent measurements. A simple, but effective way of minimizing adsorption and memory effects consists in heating all surfaces which come into contact with the substances. For this type of operation, modules having such surfaces are preferably heated to temperatures above the ambient temperature. The operating temperatures are between 50 and 200 degrees Celsius (° C.). For example, the inlet region of a mass spectrometer for the detection of explosives is usually heated to a temperature between 120° C. and 200° C., and corresponding modules of an ion mobility spectrometer are operated at temperatures between 50° C. and 100° C.

With many gas analyzers, the substances present in the gaseous phase first pass into the interior of the gas analyzer via a permeable membrane, said membrane being flushed from the outside with a sample gas containing the substances. Using a membrane made of organic polymers such as silicone rubber has the advantage that most of the organic substances to be detected pass through the membrane better than interferents or water so that, with ion mobility spectrometers in particular, a disadvantageous input of moisture is reduced. Experience has shown that a membrane inlet requires heating in order to minimize delay and memory effects in the membrane material. The delay and memory effects also occur in the gas channels leading to the ion source and in the ion source itself, and therefore gas analyzers which have a direct gas inlet instead of a membrane inlet are also affected. Moreover, it is often necessary to protect the gas analyzers used against ingress of dust, rainwater and other foreign substances. Dust filters made of wire cloth or porous materials are usually used for this purpose. These materials have relatively large surfaces in contact with the gas, and therefore low-volatility substances are adsorbed there or condense to a considerable degree, especially at low ambient temperatures.

A further reason for being able to heat modules in gas analyzers consists in keeping modules at a constant operating temperature in order to minimize temperature-dependent parameter variations, such as the permeation rate of inlet membranes. A constant operating temperature requires either means of switching between heating and cooling, which makes it necessary to have equipment of great technical complexity, or the modules must be operated permanently at a temperature above the highest ambient temperature and thus be permanently heated.

Stationary gas analyzers are supplied with energy by connecting them to a fixed power supply, where possible. Gas analyzers for mobile use are powered by electrochemical cells (disposable or rechargeable batteries), in particular by electrochemical cells with a high energy density such as lithium-manganese or lithium-ion cells. The modules operated above ambient temperature are heated electrically, which is why the electrochemical cells used for the energy supply in these cases constitute a significant proportion of the volume and weight of mobile gas analyzers.

The technical development of smaller fuel cells (FC) with powers up to a few 10 W, which are used in mobile computers and communication equipment, is far advanced. These kinds of fuel cells can also be used for mobile gas analyzers. The publication US 2004/0120857 A1 (Smith et al.) discloses a network of sensors which detect target substances at different locations and transmit measurement data to a control unit. Said sensors can be mass spectrometers and ion mobility spectrometers, for example, and the energy supply for the sensors comes from electrochemical cells or fuel cells. For use in small mobile devices, mention must be made of direct methanol fuel cells (DMFC), which achieve energy densities that exceed those of commercial electrochemical cells several times over. The direct methanol fuel cells work at an operating temperature of between 60° C. and 130° C., and have an efficiency of up to 40%.

There are other types of fuel cells apart from the DMFC. Fuel cells with electrolytes of molten salts (molten carbonate fuel cell, MCFC) are operated with hydrogen, methane or coal gas at an operating temperature of around 650 degrees Celsius and have an efficiency of 48%. For toys and science kits, magnesium-air fuel cells (MAFC), which operate with magnesium as the fuel at an operating temperature of 55 degrees Celsius and have an efficiency of up to 90%, are commercially available. To operate with hydrogen and oxygen (also oxygen from the air), there is particularly the polymer electrolyte fuel cell, also known as proton exchange membrane fuel cell (PEMFC), with polymer membranes, which operates at efficiencies of between 35% and 60% at operating temperatures of between 90 and 120 degrees Celsius. The phosphoric acid fuel cell (PAFC, 38%, 200° C.), likewise with a polymer membrane, is operated with hydrogen and air, but pure gases are not required. The alkaline fuel cell (AFC, over 60%, <80° C.) is also operated with hydrogen and air, but the air must not contain any $CO_2$. The solid oxide fuel cell (SOFC) uses carbon and oxygen at an operating temperature of 800-1000° C. and an efficiency of 47%.

The objective of the invention is to provide gas analyzers which can operate for as long as possible without a fixed power supply or in mobile use, and which have compact dimensions at the same time.

SUMMARY OF THE INVENTION

The invention provides gas analyzers which have a fuel cell and at least one module which is operated above ambient temperature and wherein the fuel cell is thermally coupled with at least one module and the waste heat from the fuel cell contributes significantly to heating at least one module. In a gas analyzer according to the invention, it is preferable for more than 20%, typically around 50% (but in some cases up to 100%), of the heating power required for one or more modules to be provided by the waste heat from the fuel cell. The module that is thermally coupled to the fuel cell can be a membrane of an inlet system, a desorption device (e.g. for swab samples), a filter (e.g., a dust filter in the inlet region of an ion mobility spectrometer), an ion source and/or an ion analyzer (e.g., a mobility or mass analyzer).

The fuel cell can generate all the electric power for the gas analyzer, said power being required not for heating modules, but in particular for the electronics or the mechanical components (such as pumps) when the analyzer is in operation. The electric power generated in the fuel cell can also be used to heat one or more modules (additional electric heating), especially for an adjustable heating system. The gas analyzer can additionally contain one or more electrochemical cells which generate part of the electric power and/or heating power. The gas analyzer can also have several fuel cells, some or all of which are thermally coupled to one or more modules.

A module coupled to the fuel cell preferably has an operating temperature of between 40 and 250 degrees Celsius. When ambient air is analyzed with an ion mobility analyzer, the operating temperature is preferably between 50° C. and 200° C. To detect explosives, the operating temperature is preferably between 120° C. and 200° C., especially when a mass analyzer or several mass analyzers are used in an $MS^n$ analysis (n=2, 3, . . . ). The fuel cell should also be thermally insulated from other modules of the gas analyzer which are not operated above ambient temperature, and can also be thermally insulated from its surroundings. The operating temperature of the fuel cell component in which the waste heat is generated is preferably at least the operating temperature of the heated module of the gas analyzer. If the operating temperature of the fuel cell is below the operating temperature of the thermally coupled module, this is electrically heated in addition. The fuel cell is preferably of the DMFC type, especially when the gas analyzer is an ion mobility spectrometer. However, it is also easily possible to use the types of fuel cell listed in the introduction.

The fuel cell can be thermally coupled to a heated module by means of a heat pipe or by means of a gas or liquid circulation system. The medium used in the heat pipe and the pressure inside the heat pipe are preferably chosen so that the boiling temperature corresponds approximately to the operating temperature of the module to be heated. The thermal coupling can also be done by means of a Peltier element connected to the fuel cell and the heated module.

Furthermore, a gas analyzer according to the invention can have a device for regulating the thermal coupling between the fuel cell and the heated module. The device can switch the thermal coupling of the fuel cell (i.e., switch it on and off) or vary it continuously so that the operating temperature of the module can be regulated. The device can make a mechanical contact between the fuel cell and the heated module, said contact being switchable or its pressing force adjustable. A further way to regulate the operating temperature of the heated module is for the gas analyzer to have a device for regulating the operating temperature of the fuel cell, or for switching a fuel cell on and off, or for regulating the output of the fuel cell. Regulation achieved by switching the fuel cell on and off is easily possible, especially when the gas analyzer has several fuel cells, or an electrochemical cell in addition, or both, in order to supply the gas analyzer with the requisite electrical operating power. The amount of heat transferred from the fuel cell to the heated module via the thermal coupling can also be varied by means of a switchable or continuously adjustable cooling system via a heat sink or heat exchanger which is thermally connected to the fuel cell and conducts waste heat from the interior of the gas analyzer to the outside. Furthermore, the module can be additionally heated electrically in order to reach the requisite module temperature and/or regulate the temperature, where the electric heating power is preferably generated by the fuel cell, or it can be connected to an adjustable heat exchanger via which heat from the module is removed to the surroundings.

The invention also provides a method for operating a gas analyzer which is operated at atmospheric pressure to detect dangerous substances and which has a fuel cell and at least one module operated above ambient temperature, where the fuel cell is used to generate the electric operating energy of the gas analyzer. The method is characterized by the fact that the waste heat from the fuel cell is used to regulate the temperature of at least one module.

DETAILED DESCRIPTION

The present invention is hereinafter described by way of example using embodiments which are depicted in FIGS. 2 to 6. The figures show the gas analyzers according to the invention schematically and not necessarily to scale. The relative dimensions and proportions of individual elements of the gas analyzers may be shown enlarged or reduced in size. The figures use the same reference numbers for the same or similar elements.

Figure 1:
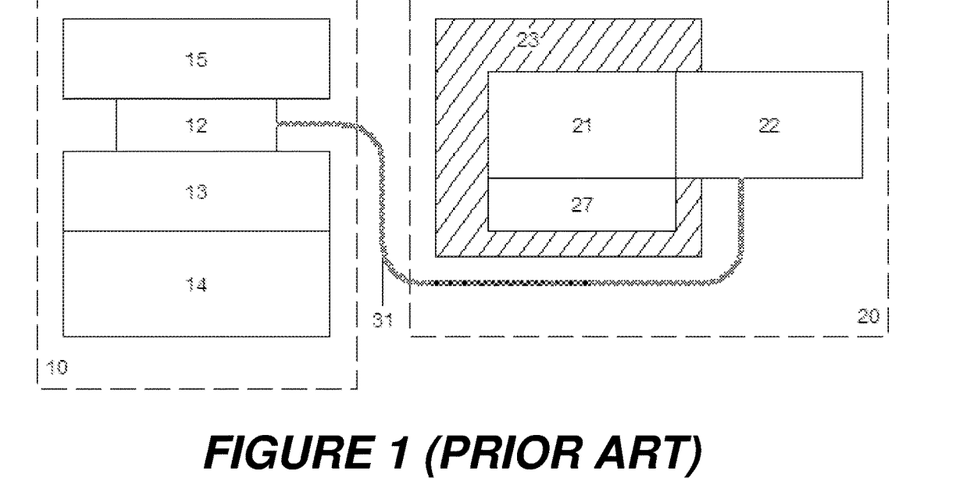
FIG. 1 shows a combination, which is known from the prior art, of a gas analyzer (20) with a separate fuel cell (10) as the power source. The gas analyzer (20) is an ion mobility spectrometer which has modules operated at ambient temperature (22) and modules operated above ambient temperature (21), which are heated by an electric heating unit (27) in order to maintain their operating temperature.

FIG. 1 shows a combination, which is known from the prior art, of a gas analyzer (20) with a separate fuel cell (10) to supply the power. The gas analyzer (20) is an ion mobility spectrometer of the drift-time type and has modules which are operated at ambient temperature (22) and modules operated above ambient temperature (21), the latter modules being heated by an electric heating unit (27) to keep them at their operating temperature. The modules (21) here include a desorption device for swab samples, a heated membrane in the inlet region to the ion source, the ion source, and the drift tube of the ion mobility spectrometer. The modules (22) comprise an ion detector, the control electronics and components of a gas circulation system of the ion mobility spectrometer.

To reduce the heating power required, the heated modules (21) and the electric heating unit (27) are surrounded by thermal insulation (23). The gas analyzer (20) is connected to the fuel cell (10) via an electric cable (31) for its power supply. A thermal connection is not intended and not necessary for the function. The electrical connection can also be established via an electric contact of any form. The fuel cell (10) comprises a reaction zone (12), in which the chemical energy of the fuel is converted into electrical energy, control electronics (13) and a fuel reservoir (14). The fuel cell can additionally comprise a pump system to supply or circulate reactants involved (not shown here).

Figure 2:
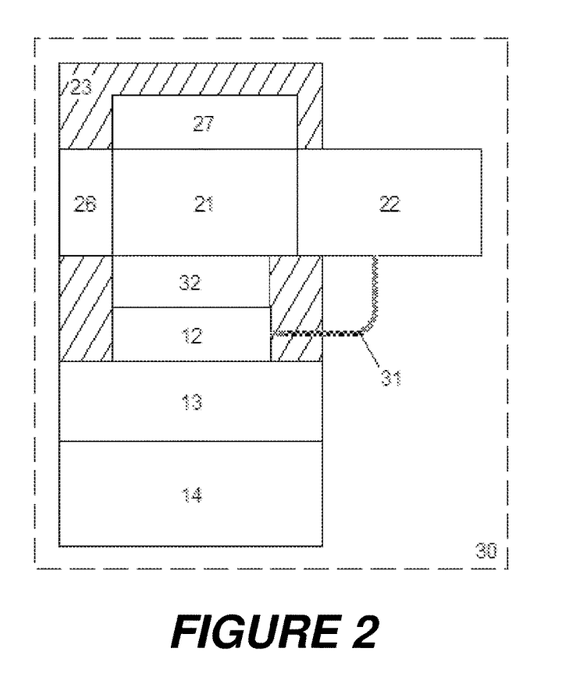
FIG. 2 shows a gas analyzer according to the invention with an ion mobility spectrometer of the drift-time type, which has modules (21) which are operated above ambient temperature and are thermally coupled via a thermal conductor (32) to the reaction zone (12) of the fuel cell.

FIG. 2 shows a gas analyzer (30) according to the invention with a fuel cell to supply power, said cell being comprised of a reaction zone (12), control electronics (13) and a fuel reservoir (14). The fuel cell can also have a (preferably adjustable) cooling device to remove some of the waste heat generated in the reaction zone (12) to the surroundings (not shown here). The fuel cell is preferably a DMFC fuel cell with an electric output of approximately 25 watts. The gas analyzer module (22) is connected to the reaction zone (12) of the fuel cell via an electrical cable (31) for its power supply.

Like the gas analyzer (20) in FIG. 1, the gas analyzer (30) is an ion mobility spectrometer of the drift-time type and likewise has modules (21) which are operated above ambient temperature. The modules (21) likewise include a desorption device for swab samples, a heated membrane in the inlet region to the ion source, the ion source, and the drift tubes of the ion mobility spectrometer. The modules (21) are thermally coupled to the reaction zone (12) of the fuel cell via a heat conductor (32). Thus, the waste heat from the fuel cell, which is generated in the reaction zone (12) when the chemical energy is converted into electrical energy, is used for heating the modules (21). The heat conductor (32) here is a solid (e.g., a strip or profile) made of materials with good thermal conductivity such as copper or aluminum, and the heat is transferred via diffuse thermal conduction. Alternatively, thermal coupling can also take place via thermal convection with the aid of liquid or gaseous heat transfer media, or via a heat pipe in which the heat is transferred by vaporization and condensation.

The reaction zone (12) of the fuel cell, the thermal conductor (32) and the modules (21) of the ion mobility spectrometer are enclosed by thermal insulation (23) in order to minimize the thermal losses to the surroundings and thus use as much of the fuel cell's waste heat as possible to heat the modules (21). The control electronics (13), the fuel reservoir (14) of the fuel cell, and the modules operated at ambient temperature (22), comprising the ion detector, the control electronics and components of a gas circulation system of the ion mobility analyzer, are preferably located outside the thermal insulation to avoid subjecting them to a thermal load.

The equilibrium temperature of the heated modules (21) of the gas analyzer (30) adjusts itself, without any additional heating or cooling, to a value between the ambient temperature and the operating temperature of the fuel cell's reaction zone (12). A low thermal resistance of the thermal conductor (32) and a high thermal resistance of the thermal insulation (23) with respect to the surroundings shift the temperature of the module (21) to higher temperatures. For a given electrical output of the fuel cell and the associated heating power, the temperature of the heated modules (21) can be preset to a specific temperature difference relative to the ambient temperature by choosing a suitable thermal resistance of the thermal conductor (32) and a suitable thermal resistance of the thermal insulation (23) with respect to the surroundings. The temperature of the heated modules (21) is thus above the ambient temperature and varies with the ambient temperature.

It is often necessary or desirable to keep the temperature of the heated modules (21) constant or at least within a specific temperature range. The gas analyzer (30) has a cooling device (26) as well as an additional electric heating unit (27), which are used in combination or alternatively depending on the ambient temperature, in order to operate the gas analyzer (30) in a wide range of ambient temperatures and at a constant target temperature of the modules (21). When the temperature of the modules (21) is above a predetermined target temperature, the additional cooling device (26) removes the excess heat to the surroundings. The cooling device (26) here has a cooling surface or heat sink in contact with the ambient air and a variable-speed fan, which feeds a variable amount of ambient air to the cooling surface or the heat sink. When the temperature of the modules (21) is below the predetermined target temperature, the modules (21) are additionally heated by the additional electric heating unit (27). The additional heating unit (27) is powered by the fuel cell just like the other electrical components of the gas analyzer (30). There is the option to supply the additional heating and cooling via a Peltier element, which is operated in the appropriate polarity and is thermally connected to the surroundings.

Table 1 shows typical data for the energy requirement of the gas analyzer (20) from the prior art and the gas analyzer (30) according to the invention, where both gas analyzers have an ion mobility spectrometer with a heated membrane inlet, and operating times derived from this.

Lines 1 to 6 of Table 1 contain typical values of a DMFC fuel cell. Lines 7 and 8 give the power consumption of an ion mobility spectrometer with a heated inlet membrane at the lower limit of the ambient temperature. For gas analyzers with heated modules, it is quite typical that the heating power requirement makes up a significant proportion, sometimes even the majority, of the total energy requirement. Line 9 indicates that, based on the assumed 21% efficiency, the waste heat produced by the fuel cell is greater than the electric power it provides. Up to here, the values for a separate and a thermally coupled fuel cell are the same.

In Line 10, it is assumed for the gas analyzer according to the invention with a thermally coupled fuel cell that 50% of the waste heat can be used to heat the heated modules (21), in particular the inlet membrane. The thermal coupling can be simply achieved by bringing the reaction zone (12) of the fuel cell into thermal contact with one of the heated modules (21) by means of a strip of copper braiding. The remaining waste heat from the fuel cell is removed to the surroundings. When operating the separately located fuel cell without thermal coupling, the waste heat is not used to heat modules, but removed in its entirety to the surroundings so that the proportion of waste heat used here is zero.

The different waste heat utilization factors result in different values for the additional electric power needed to heat the inlet membrane. With the thermally coupled fuel cell, part of the waste heat which results from supplying the electric power for the additional heating is used directly to heat the inlet membrane (Line 11). The electric power consumption of the electronics and the heating of the inlet membrane is only 8.68 W with thermal coupling and 25 W without coupling (Line 12), which results in operating times (Line 13) of 41 and 14 hours respectively with a usable electrical energy of 353 Wh (Line 6). A gas analyzer (30) according to the invention with thermal coupling has therefore almost three times the operating time of a gas analyzer (20) from the prior art. In addition, the waste heat removed to the surroundings is reduced by the same factor.

Figure 3:
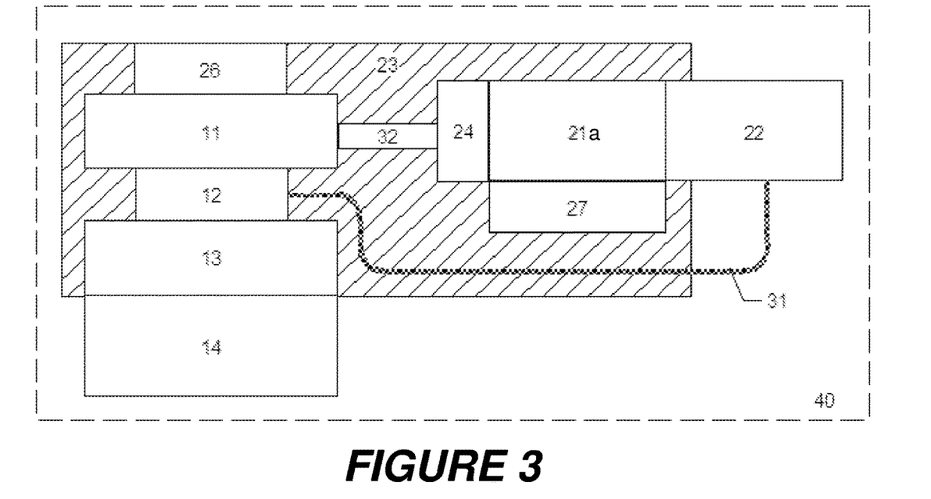
FIG. 3 depicts a gas analyzer (40) according to the invention with a heated mobility analyzer (21a) which is thermally coupled to the reaction zone (12) of a fuel cell via two heat couplers (11, 24) and a heat pipe (32).

FIG. 3 depicts a gas analyzer (40) according to the invention with a heated mobility analyzer (21a), which is

TABLE 1

| Line | Power source | DMFC 25 W arranged separately (as in FIG. 1) | DMFC 25 W thermally coupled (as in FIG. 2) |
|---|---|---|---|
| 1 | Energy density per unit mass (kWh/kg) | 5.6 | 5.6 |
| 2 | Mass when empty (kg) | 0.36 | 0.36 |
| 3 | Mass of the fuel (kg) | 0.3 | 0.3 |
| 4 | Total mass of the fuel cell (kg) | 0.66 | 0.66 |
| 5 | Efficiency of the fuel cell | 0.21 | 0.21 |
| 6 | Usable electrical energy (Wh) | 353 | 353 |
| 7 | Electric power consumption of the electronics (W) | 5.00 | 5.00 |
| 8 | Power consumption of the inlet membrane heating (W) | 20.00 | 20.00 |
| 9 | Waste heat from the fuel cell (W) which is generated through supplying the electronics | 18.81 | 18.81 |
| 10 | Waste heat from the fuel cell (W) which is used for heating the inlet membrane | 0 | 9.40 |
| 11 | Additional power (W) required to heat the inlet membrane, made up of | 20.00 | 10.60 |
|  | electric power (W) | 20.00 | 3.68 |
|  | utilized waste heat from the fuel cell (W) | 0.00 | 6.92 |
| 12 | Electric power consumption of the electronics and the inlet membrane heating (W) | 25.00 | 8.68 |
| 13 | Operating time (h) | 14.11 | 40.66 | thermally coupled to the reaction zone (12) of a fuel cell via two heat couplers (11, 24) and a heat pipe (32).

Heat pipes transport thermal energy by vaporizing a liquid at the heat source, transporting the vapor, condensing it at the heat sink and returning the liquid by capillary forces. To this end, the inner wall of a heat pipe is usually provided with a porous sintered material or with a braid, usually of metal. The thermal conduction is orders of magnitude higher than that of the best conducting metals. However, this applies only as long as the temperature of the modules to be heated is below the condensation temperature of the heat transfer medium.

The fuel cell here is a DMFC fuel cell, which is preferably operated at a temperature between 90° C. and 120° C. The target temperature of the mobility analyzer is around 80° C. The boiling point of the heat transfer medium is chosen so as to prevent the mobility analyzer (21a) from overheating. The heat couplers (11, 24) couple the heat pipe (32) to the reaction zone (12) and the mobility analyzer (21a) and consist of a metal with good thermal conductivity, such as Ag, Cu or Al. Within the heated modules of the mobility analyzer (21a), the heat is transferred by conduction via the wall or, if the wall materials have low thermal conductivity, via an additional sheath made from a material with sufficiently good thermal conductivity.

The mobility analyzer (21a), the heat pipe (32), the heat couplers (11, 24) and the reaction zone (12) of the fuel cell are enclosed by thermal insulation (23) made of a material with low thermal conductivity, preferably compacted glass wool or rock wool, in order to utilize the waste heat effectively. The thickness of the thermal insulation is preferably chosen so that the waste heat from the fuel cell generated by the power supply to the gas analyzer is just sufficient to heat the mobility analyzer (21a) to 80° C., given an ambient temperature of 20° C. (room temperature).

When the thermal insulation is dimensioned in this way, an additional supply of heat is required via the additional electric heating unit (27) in order to keep the operating temperature of the mobility analyzer (21a) constant if the ambient temperature is below 20° C. The power of the additional heating (27) is automatically reduced down to zero with increasing ambient temperature. To prevent the mobility analyzer (21a) overheating at ambient temperatures above 20° C., the gas analyzer (40) has a cooling device in the form of a fan (26), which is arranged in a cutout of the thermal insulation (23) and, when it is in the active state, blows toward the heat coupler (11) in the reaction zone (12). For ambient temperatures where no additional heating (27) is necessary, the temperature of the mobility analyzer (21a) is controlled by regulating the air flow of the fan (26).

The fuel reservoir (14) is preferably an exchangeable cartridge and located outside the thermal insulation (23) for easier access.

Figure 4:
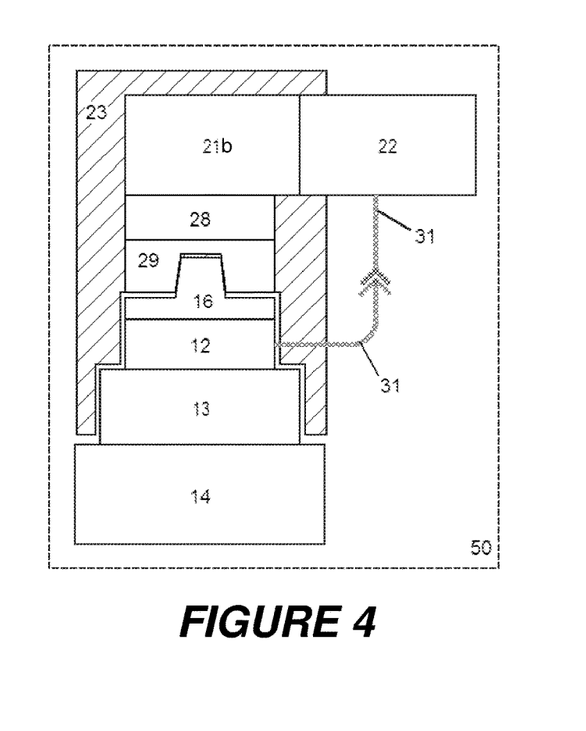
FIG. 4 illustrates a gas analyzer (50) according to the invention with an ion mobility spectrometer which has a heatable inlet membrane (21b) and unheated modules (22), where the inlet membrane (21b) is thermally coupled to the reaction zone (12) of a fuel cell via a Peltier element (28) and two plug-in connections (16, 29).

FIG. 4 depicts a gas analyzer (50) according to the invention with an ion mobility spectrometer which has a heatable inlet membrane (21b) and unheated modules (22). The operating temperature of the inlet membrane (21b) is 60° C. The gas analyzer (50) also has an additional heating unit (28), a heat coupler in the form of a female plug-in connector (29) and a low-temperature DMFC (direct methanol fuel cell) or a low-temperature DEFC (direct ethanol fuel cell). The fuel cell comprises a reaction zone (12), a heat coupler in the form of a male plug-in connector (16), the control electronics (13) and a fuel tank (14).

The plug-in connections (16, 29) providing the thermal coupling can be mechanically coupled with an electrical connection (31) which connects the reaction zone (12) of the fuel cell electrically with the modules of the ion mobility spectrometer. At least one of the electrical contacts of the fuel cell here is designed so that it creates the thermal as well as the electric coupling between the fuel cell and the modules of the gas analyzer (50). The gas analyzer (50) is connected electrically to ground via the thermal plug-in connections (16, 29), while the second operating voltage connection is done via a separate plug-in connection in the cable (31). Constructing the thermal and electrical connection of the modules as plug-in contacts allows the gas analyzer (50) to have a variety of power supply options—suitable fuel cells as well as rechargeable and primary cell packs or a power supply module for connection to a fixed power supply.

The plug-in connections (16, 29) can be coaxial plug-in connections with sufficient thermal conductivity. They are then constructed like the high-frequency plug-in connectors used to transfer higher powers, but can also have the form of solid metal contact pins and contact sockets arranged in parallel, or of spring-loaded flat contacts made of materials with good electrical and thermal conductivity.

The low-temperature DMFC and DEFC fuel cells preferably used in the gas analyzer (50) already achieve high efficiencies at operating temperatures of 30° C.-50° C. Since these temperatures are below the 60° C. operating temperature of the inlet membrane (21b), additional electric heating of the inlet membrane (21b) via the additional electric heating unit is required. The temperature difference means a heat flux is generated from the heated inlet membrane (21b) to the reaction zone (12) of the fuel cell, which can lead to thermal losses at the inlet membrane (21b) and to the fuel cell heating up so that the cell is operated outside the range with the highest efficiency. The fuel cell is prevented from heating up by arranging a Peltier element (28) between the thermal plug-in connections (16, 29) and the heated inlet membrane (21b) and using it as additional heating. When an electric current flows in a given direction through the Peltier element (28), one side is heated and the other one cooled at the same time, as happens in a heat pump. The heated side of the Peltier element (28) is connected to the inlet membrane, which requires heating (21b), and the cooled side is connected to the plug-in connections (16, 29). The current flow through the Peltier element (28) brings about an electrically induced thermal flux from the cooled to the heated side which exceeds the parasitic heat flux in the opposite direction because of the thermal resistance of the Peltier element (28).

The effective efficiency of a Peltier element (28) is 10%-20%. This means that 10%-20% of the electric power utilized is removed as heat from the fuel cell and the fuel cell is cooled. On the other hand, the electric power utilized as well as the thermal power removed from the other side is available on the hot side of the Peltier element (28) to heat the inlet membrane (21b) so that the efficiency as heating relative to the electric power used is even greater than 1. This corresponds to the operating mechanism of a heat pump, which uses electrical energy to transport heat from the side at the lower temperature to the side at the higher temperature. The thermal diffusion toward the fuel cell under the influence of the temperature gradient is thus overcompensated by the electrothermal heat transport of the Peltier element (28) toward the inlet membrane (21b). The fuel cell can be operated at its optimum temperature and supplies heat to the inlet membrane (21b) operated at a higher temperature at the same time.

Figure 5:
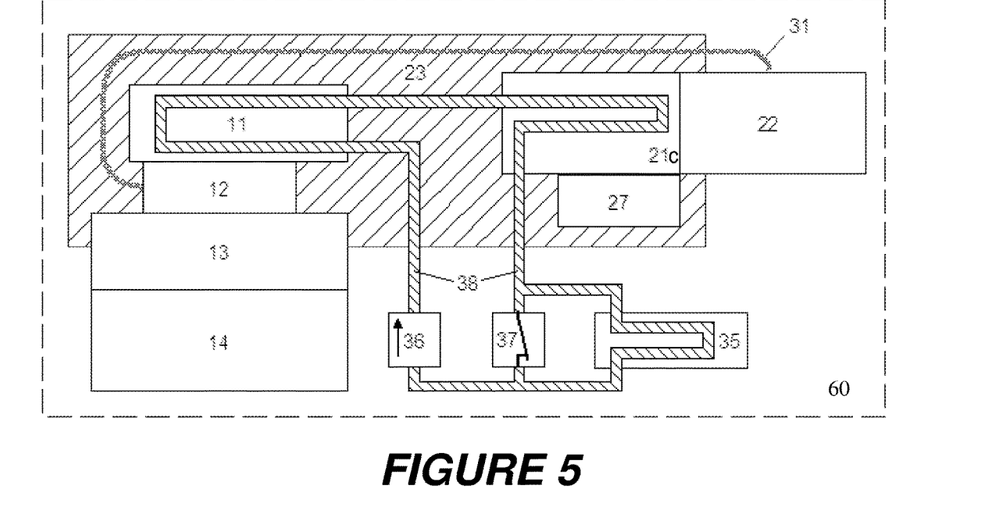
FIG. 5 depicts a gas analyzer (60) according to the invention with a mass spectrometer which has a heated inlet block (21c) and unheated modules (22). The waste heat produced in a fuel cell battery is removed from the reaction zone (12) of the fuel cells with the aid of a heat exchanger (11) via a liquid circulation system and conducted to the inlet block (21c).

FIG. 5 shows a gas analyzer (60) according to the invention with a mass spectrometer, e.g., of the quadrupole filter or ion trap type. The mass spectrometer has a heated inlet block (21c) and unheated modules (22).

The inlet block (21c) contains a heated inlet capillary connected to the surroundings, which is followed by a multi-stage system of diaphragms to gradually reduce the pressure from the ambient pressure down to the operating pressure of the mass analyzer. The inlet capillary and the downstream system of inlet diaphragms are heated to a temperature of 150° C.-200° C. to prevent substances condensing and are housed in the heated inlet block (21c) for this purpose. The inlet block (21c) provides the thermal coupling of the mass spectrometer components that require heating, and also contains a number of channels which are connected with each other and filled with a liquid heat transfer medium.

The gas analyzer (60) furthermore contains a battery of phosphoric acid fuel cells, which are operated at a temperature of around 200° C. The hydrogen needed to operate the phosphoric acid fuel cells is provided via a small pressurized bottle. Such pressurized bottles between 0.2 and 2 liters are commercially available for operating mobile gas chromatographs, for example. The oxygen can be taken from the air. The phosphoric acid fuel cell is undemanding as far as the purity of the air is concerned, so stable operation is achieved without complex filtering of the air. The phosphoric acid fuel cell does not provide a very high current density and therefore cannot be built so as to be extremely compact. This is not critical, however, given the size of a mass spectrometer with a pump system.

The pump system and the heating of the inlet block (21c) by themselves mean that the power required by the mass spectrometer is usually above 20 W. The waste heat produced in the fuel cells is removed from the reaction zone (12) with the aid of a heat exchanger (11) via a liquid circulation system and conducted to the inlet block (21c). The heat exchanger (11) is closely connected thermally to the reaction zone (12) of the fuel cell. The lines (38) connect the connections of the inlet block (21c), the heat exchanger (11) and a circulation pump (36) to a closed liquid circulation system, which is filled with silicone oil, for example. Between the exit of the inlet block (21c) and the heat exchanger (11), the liquid circulation system furthermore contains a chiller (35) and a thermostatic valve (37), which is open below a predetermined temperature of the liquid, thus bypassing the chiller (35). The switching point of the thermostatic valve (37) is set to 180° C. to 200° C. so that the liquid flows through the chiller (35) only when it is above this temperature and the chiller (35) can perform its cooling effect. The chiller (35) itself is located inside a cooling duct in the gas analyzer (60) and is cooled with ambient air with the aid of a fan, where necessary.

At low ambient temperatures, where the waste heat from the fuel cell is not sufficient to heat the inlet block (21c) up to the operating temperature, the inlet block (21c) is heated by an additional electric heating unit (27), which is powered electrically by the fuel cell.

The heated inlet block (21c), the reaction zone (12), the heat exchanger (11) and the additional electric heating unit are enclosed in thermal insulation (23).

It shall be understood that the circulation system can fundamentally also be operated with a gas instead of a liquid as its working medium.

Figure 6:
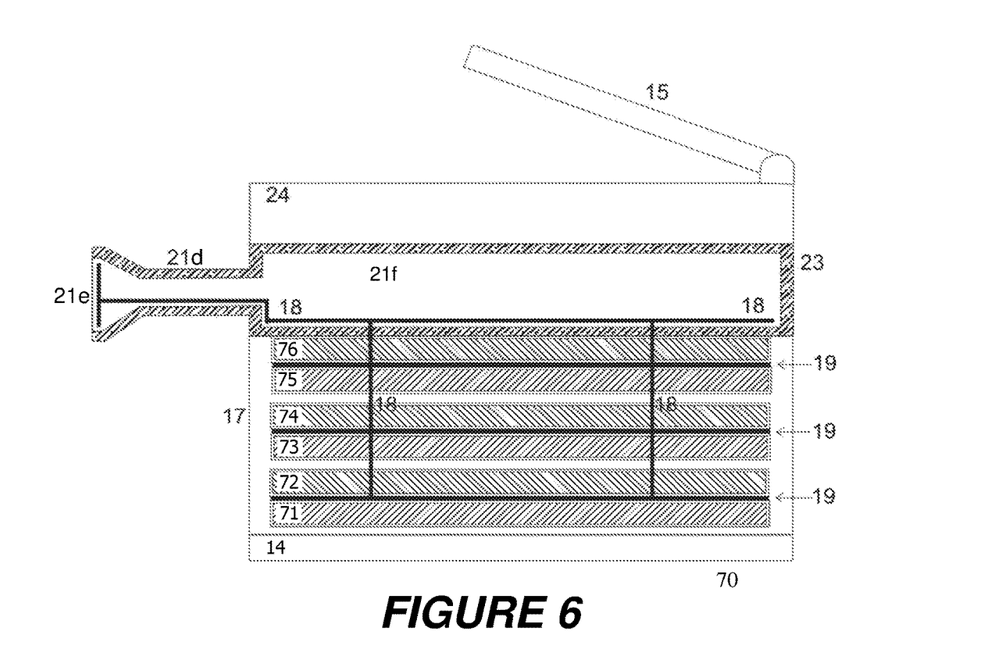
FIG. 6 shows the schematic set-up of an ion mobility spectrometer (70) in an embodiment with a heated sensing probe (21d), which vaporizes particles by means of a heated membrane (21e), the vapors being fed into a mobility analyzer (21f). The waste heat from DMFC fuel cells (71 to 76) is taken up by thin copper plates (19) and conducted to the mobility analyzer (21f) and the sensing probe (21d) by a system of heat pipes (18).

FIG. 6 shows the schematic design of an ion mobility spectrometer (70) in an embodiment with a heated sensing probe (21d), which vaporizes particles by means of a heated membrane (21e). The vapors are fed to a mobility analyzer (21f). A methanol tank (14) supplies the DMFC fuel cells (71 to 76) with methanol as their fuel. The tank (14) here can be refilled from the outside or exchanged for another.

The membrane (21e) can be made from silicone material in a known way, for example; silicone membranes absorb organic substance vapors and release them again at their rear surface. The sensing probe of the ion mobility spectrometer (70) can be pressed onto a suspect surface (or onto a swab sample) and indicates the presence of drugs, explosives, or other substances on the surface via an appropriate alarm. The surface can be the outside of a suitcase, the lining of an automobile trunk, or even the surface of the clothing of a suspicious person.

The DMFC has the advantage that the methanol fuel can be easily refilled because it is not pressurized like hydrogen, for example. Cartridges of methanol which can easily be used are already on the market. The cartridges are even approved for carriage aboard passenger planes. DMFC batteries are normally operated with approximately 30 percent methanol in water; DMFC chargers for cell phones are already on the market which are operated with 99 percent methanol and supply a voltage of 5.4 volts and a power of 9 watts with dimensions of 150×56×19 cubic millimeters.

The waste heat from the fuel cells (71 to 76) is taken up by thin copper plates (19), and conducted to the mobility analyzer (21f) and the sensing probe (21d) through a system of heat pipes (18). The mobility analyzer (21f) and the sensing probe (21d) are enclosed by an insulating layer (23). Air is fed to the fuel cells (71 to 76) within the housing (17). Above the mobility analyzer (21f) is an electronic system (24) with a display unit (15). The instrument weighing approximately one kilogram can be held with handles (not shown) and the sensing probe (21d) can be pressed against a surface to analyze adhering particles or adsorbed substances.

The ion mobility spectrometer (70) is preferably designed as a sandwich construction: A fuel cell at the bottom supports the mechanical part of the mobility analyzer (21f); above this are the thermally insulated electronics for the power supply, measurement, data processing and display. This means that the fuel cell is freely accessible for refilling with fuel, for example. When it is well heated, the ion mobility spectrometer (70) can be maintained at a favorable temperature of between 100 and 200 degrees Celsius, preferably between 150 and 180 degrees Celsius. The electronics, on the other hand, can be cooled by insulating them and conducting the heat to the outside.

The battery of fuel cells (71 to 76), which supply a voltage of approximately six volts when connected together, supports above it the mechanical part of the mobility analyzer (21f), which should be kept in a heated state so that no substances can condense. This mechanical part comprises firstly an inlet section (21d) to feed in the substance vapors for analysis, here with a sensing probe membrane (21e), and secondly the mobility analyzer (21f) with ion source, drift tube and detector (not drawn individually). The mobility analyzer (21f) can be accommodated together with an air filter and recirculating air pump in a volume of around 8×16×4 cubic centimeters and protected against thermal losses with an insulating layer (23).

The methanol tank (14) is located underneath the fuel cell battery (71 to 76). This arrangement makes the fuel cell battery (71 to 76) with tank (14) freely accessible for refilling with fuel or exchanging the tank (14), for example. The electronics (24), on the other hand, can be sufficiently well cooled by insulating them and conducting the heat to the outside. In operation, the electric power requirement of the ion mobility spectrometer (70) is only approximately 10 to 20 watts.

The invention claimed is:

1. Gas analyzer with a fuel cell and at least one module which is operated above ambient temperature, wherein the fuel cell is thermally coupled to the at least one module and waste heat from the fuel cell contributes to heating the at least one module to a temperature above ambient.

2. The gas analyzer according to claim 1, wherein more than 20% of the heating power required for the module is provided by the waste heat from the fuel cell.

3. The gas analyzer according to claim 1, wherein the module is a membrane of an inlet system, a desorption device, a filter, an ion source and/or an ion analyzer.

4. The gas analyzer according to claim 1, wherein the module has an operating temperature between 40 and 250 degrees Celsius.

5. The gas analyzer according to claim 1, wherein the fuel cell is thermally coupled to the module via a heat pipe or a liquid circulation system.

6. The gas analyzer according to claim 1, wherein the gas analyzer has a Peltier element which is thermally coupled to the fuel cell and the module.

7. The gas analyzer according to claim 1, wherein the gas analyzer has a device to regulate the thermal coupling between the fuel cell and the module.

8. The gas analyzer according to claim 7, wherein the device switches or continuously varies the thermal coupling of the fuel cell.

9. The gas analyzer according to claim 7, wherein the device makes a mechanical contact between the fuel cell and the module, said module being switchable or its pressing force adjustable.

10. The gas analyzer according to claim 1, wherein the gas analyzer has a device to regulate the operating temperature of the fuel cell or to regulate or switch the fuel cell on/off.

11. The gas analyzer according to claim 1, wherein the gas analyzer has an additional electric heating unit which is thermally coupled to the module.

12. The gas analyzer according to claim 1, wherein the gas analyzer has a cooling device which is thermally coupled to the module.

13. The gas analyzer according to claim 1, wherein the module is thermally insulated from other modules of the gas analyzer which are not operated above ambient temperature.

14. The gas analyzer according to claim 1, wherein the gas analyzer is an ion mobility spectrometer or mass spectrometer for mobile use.

15. Method for operating a gas analyzer which is operated at atmospheric pressure to detect dangerous substances and has a fuel cell and at least one module operated above ambient temperature, wherein the fuel cell is used to generate electrical operating power of the gas analyzer and wherein waste heat from the fuel cell is used to regulate a temperature of the at least one module.

* * * * *